US010503573B2

(12) United States Patent
Lai

(10) Patent No.: US 10,503,573 B2
(45) Date of Patent: Dec. 10, 2019

(54) INTERNAL SIZING/LANE STANDARD SIGNAL VERIFICATION

(75) Inventor: Ching Ming Lai, Wakefield, MA (US)

(73) Assignee: ANALOGIC CORPORATION, Peabody, MA (US)

( * ) Notice: Subject to any disclaimer, the term of this patent is extended or adjusted under 35 U.S.C. 154(b) by 854 days.

(21) Appl. No.: 13/704,007

(22) PCT Filed: Jun. 29, 2010

(86) PCT No.: PCT/US2010/040283
§ 371 (c)(1),
(2), (4) Date: Dec. 13, 2012

(87) PCT Pub. No.: WO2012/002930
PCT Pub. Date: Jan. 5, 2012

(65) Prior Publication Data

US 2013/0090861 A1 Apr. 11, 2013

(51) Int. Cl.
*G06F 11/00* (2006.01)
*G16B 99/00* (2019.01)
*G16B 20/00* (2019.01)
*G16B 40/10* (2019.01)

(52) U.S. Cl.
CPC .............. *G06F 11/00* (2013.01); *G16B 20/00* (2019.02); *G16B 40/10* (2019.02); *G16B 99/00* (2019.02)

(58) Field of Classification Search
None
See application file for complete search history.

(56) References Cited

U.S. PATENT DOCUMENTS 5,419,825 A * 5/1995 Fujii ................ G01N 27/44721 204/608
6,274,317 B1 8/2001 Hiller et al.
6,991,713 B2 1/2006 Adourian et al.
2005/0042668 A1* 2/2005 Perlin .............................. 435/6
2009/0228245 A1 9/2009 Gilbert et al.

FOREIGN PATENT DOCUMENTS

WO WO 0208949 A2 * 1/2002
WO 2009/156741 A1 12/2009
WO 2010/029309 A1 3/2010

OTHER PUBLICATIONS

International search report for PCT/US2010/040283 published as WO 2012/002930 A1 .
Butler, Forensic Data Typing Biology, Technology, and Genetics of STR Markers. 2005, Elsevier Academic Press, abstract attached.
International Written Opinion received for PCT Patent Application No. PCT/US2010/40283, dated Apr. 6, 2011, 8 pages.
European Office Action received for European Application No. 10729758.2, dated Dec. 19, 2016, 10 pages.
European Office Action received for European Application No. 10729758.2, dated Aug. 14, 2018, 7 pages.
Applied Biosystems: "GeneMapper ID SoftwareVersion 3.1", Dec. 1, 2003 (Dec. 1, 2003), pp. FP-VIII, 7-1-7-27, B-1-B36, XP002741907, Retrieved from the Internet: URL:https://tools.lifetechnologies.com/content/sfs/manuals/cms/041338.pdf retrieved on Jul. 7, 2015 pp. 7-1-7-25, B1-B36.
Applied Biosystems: "AmpFISTR SGM Plus Amplification Kit", Aug. 1, 2012 (Aug. 1, 2012), pp. 1-18, XP002741908, Retrieved from the Internet : URL: https://www3.appliedbiosystems.com/cms/group/applied_markets_support/documents/generaldocuments/cms_041049.pdf retrieved on Jul. 7, 2015 p. 11-18.

* cited by examiner

*Primary Examiner* — G Steven Vanni
(74) *Attorney, Agent, or Firm* — TraskBritt

(57) ABSTRACT

A method for verifying an ILS signal for DNA processing includes obtaining the ILS signal, determining acquisition times between peaks of the ILS signal, obtaining acquisition times between peaks in reference ILS information for the ILS signal, and verifying the ILS signal based on the ILS acquisition times and the reference ILS acquisitions times. An ILS signal processor includes a false peak remover that removes any false peaks in an ILS signal and a signal verifier that verifies the ILS signal includes only true peaks based on reference ILS information for the ILS signal.

19 Claims, 9 Drawing Sheets

INTERNAL SIZING/LANE STANDARD SIGNAL VERIFICATION

CROSS-REFERENCE TO RELATED APPLICATION

This application is a national phase entry under 35 U.S.C. § 371 of International Patent Application PCT/US2010/040283, filed Jun. 29, 2010, designating the United States of America and published in English as International Patent Publication WO 2012/002930 A1 on Jan. 5, 2012.

TECHNICAL FIELD

The following generally relates to DNA analysis and finds particular application to verifying the internal sizing/lane standard signal used to translate an acquisition time of a DNA signal into a corresponding DNA fragment size.

BACKGROUND

DNA sequencing is a method for determining the order of the nucleotide bases (adenine, guanine, cytosine, and thymine) in a sample including DNA. With one technique, the DNA is lysed, and fragments thereof containing alleles, or short tandem repeat (STR) sequences of the four nucleotides, are replicated through polymerase chain reaction (PCR). A reference substance containing synthesized fragments of known fragment sizes is added to the sample containing the replicated fragments. These fragments of known size have been referred to as internal sizing standards or internal lane standard (ILS) fragments.

The DNA and ILS fragments are labeled with different target specific fluorescent dyes (e.g., one for each nucleotide base and one for the ILS fragment) and separated through electrophoresis. In one instance, this includes applying a high voltage across negative and positive electrodes of a capillary carrying the labeled fragments. A net electric field exerts an electrostatic force on the surface charge of the labeled fragments, and the labeled fragments migrate through the capillary at a speed that depends on the size of the fragment and/or other factors.

Theoretically, fragments of the same size should migrate and arrive at a reading region at about the same time. For reading, a light beam having a wavelength within a predetermined wavelength range irradiates and excites the dyes of the fragments, and an optical reader senses characteristic fluorescent light emitted by the dyes and generates electrical signals indicative of the characteristic fluorescent light, including DNA and ILS signals. The characteristic fluorescent light allows for separating the fragments by nucleotide base and ILS sub stance.

However, the migration time of the DNA and ILS fragments varies from one lane to another lane of a biochip and from one run to another run in different biochips for various reasons. As a consequence, the fragment sizes cannot be determined simply from the acquisition time of the peaks in the signal. On the other hand, the ILS substance contains only fragments of known sizes and migrates in the same manner as the DNA fragments. As such, the ILS signal can be used to translate the acquisition times of the DNA fragments into fragment sizes. Unfortunately, the ILS signal may include false peaks and/or missing peaks, which may lead to erroneous translation and sequencing.

Furthermore, there is a small offset between the calculated fragment size and the true DNA fragment size, and this offset may differ among alleles and from run to run. To correct for these offsets, a substance that contains virtually all possible DNA fragments is processed alone in a separate lane. The signal of this substance is called an allelic ladder signal, and it is detected like the DNA sample. Each peak in the ladder signal indicates the expected peak position for the DNA fragment, and the allele number can be accurately determined by matching the peak in DNA signal to the peaks in the ladder signal. However, similar to the ILS signal, the allelic ladder signal may include false peaks and/or missing peaks, which can lead to erroneous matching.

BRIEF SUMMARY

Aspects of the application address the above matters, and others.

In one aspect, a method for verifying an ILS signal for DNA processing includes obtaining the ILS signal, determining acquisition times between peaks of the ILS signal, obtaining acquisition times between peaks in reference ILS information for the ILS signal, and verifying the ILS signal based on the ILS acquisition times and the reference ILS acquisitions times.

In another aspect, an ILS signal processor includes a false peak remover that removes any false peaks in an ILS signal and a signal verifier that verifies the ILS signal includes only true peaks based on reference ILS information for the ILS signal.

In another aspect, a computer readable storage medium encoded with computer executable instructions, causes, when the instructions are executed by a processor of a computer, the processor to: identify and remove any false peaks an ILS signal based on deviations of acquisition times between peaks in the ILS signal and acquisition times between peaks in reference ILS information.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
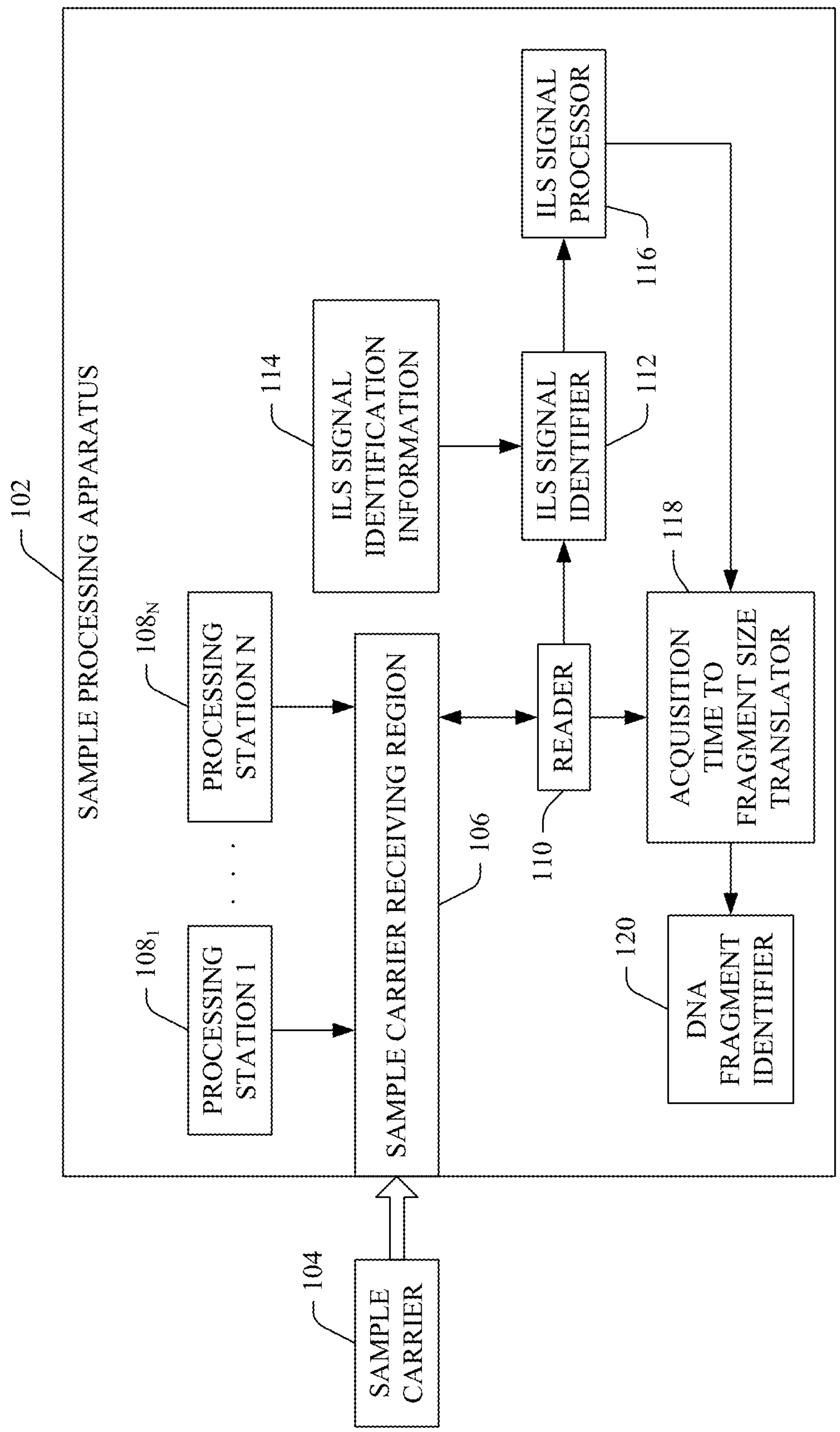
FIG. 1 illustrates an example sample processing apparatus for processing one or more samples of a sample carrier.

FIG. 1 illustrates a sample processing apparatus 102 for processing one or more samples of a sample carrier 104. An example of a suitable sample carrier 104 includes, but is not limited to, a biochip, a lab-on-a-chip, and/or other sample carriers carrying a bio or non-bio sample. Such a sample carrier 104 may include a plurality of micro-channels or lanes for carrying and moving a plurality of different samples through multiple different processing regions of the sample carrier 104, for example, during parallel processing of the samples thereon. Micro-fluidics and/or other technology can be used to move a sample from processing region to processing region, a reagent to a processing region, etc.

In the illustrated example, the sample carrier 104 carries DNA samples to be processed. Such processing includes, but is not limited to, lysing the DNA, adding a primer to the lysed DNA, replicating/amplifying one or more DNA fragments, labeling the DNA fragments with target (nucleotide base) specific fluorescent dyes respectively having different wavelengths of fluorescence and emission, adding a fluorescent dye (having yet another different wavelength of fluorescence and emission) labeled internal lane (or sizing) standard (ILS) substance with fragments of known sizes, separating the DNA, ILS and allelic ladder fragments, and/or other processing. In another embodiment, the sample carrier 104 carries another type of sample, including DNA and non-DNA samples.

The illustrated sample processing apparatus 102 is configured to process at least samples of DNA, including, but not limited to sequencing nucleotide bases (adenine, guanine, cytosine, and thymine) or determining alleles in a sample carried by the sample carrier 104. The sample processing apparatus 102 includes a sample carrier receiving region 106 that is configured to receive the sample carrier 104.

The sample processing apparatus 102 also includes one or more processing stations $\mathbf{108}_1, \ldots, \mathbf{108}_N$ (wherein N is an integer equal to or greater than one), collectively referred to herein as processing stations 108. The sample processing apparatus 102 generally carries out three basic operations, namely, purification of the sample, replication of the DNA fragments through PCR, and the separation and detection of the fragments. In the illustrated embodiment, the processing stations 108 include at least an electrophoresis processing station as the means of separating the fragments. This processing station is used to apply an electric field across the sample, which causes the DNA fragments, ILS fragments and allelic ladder fragments to move or migrate and separate at different rates through the electrophoresis processing region based on fragment size.

The sample processing apparatus 102 also includes a reader 110 that analyzes the separated fragments. The illustrated reader 110 includes at least an optical reader that directs a light beam of a predetermined wavelength range at the labeled fragments, senses the light emitted by the dyes in response to the emitted light, and generates a signal indicative of the sensed light. As noted above, each target specific dye has a different wavelength of fluorescence and emission and thus the signal is indicative of the corresponding nucleotide base and ILS sub stance.

An ILS signal identifier 112 identifies the signal (hereafter the ILS signal) corresponding to the ILS substance. In the illustrated embodiment, the ILS signal identifier 112 identifies the ILS signal based on ILS signal identification information 114, which may include information about the spectral characteristics of the fluorescent dye attached to the ILS substance and those attached to the DNA sample. The information is used to separate ILS signal from DNA fragment signals in the process commonly known as color separation. It also includes the key information about the distinct number and size of the fragments in the ILS substance. One or more components can be used to remove artifacts, such as distorted baseline and instrumental errors, spikes with very narrow width in the peak shape, peaks that are too wide, too narrow, or too skew, etc.

An ILS signal processor 116 processes the ILS signal. As described in greater detail below, in one embodiment the ILS signal processor 116 verifies that the ILS signal only includes true peaks and/or identifies and removes false peaks when the ILS signal includes one or more false peaks. Where the ILS signal is missing peaks, the ILS signal processor 116 rejects the ILS signal. In another embodiment, the ILS signal processor 116 verifies that the allelic ladder signal only includes true peak and does not include false peaks.

An acquisition time to fragment size translator 118 translates the acquisition times of the DNA fragments into fragment sizes (e.g., in units of base pairs, where a base pair is the size of a pair of DNA nucleotides). Generally, the migration speed of the DNA fragments during electrophoresis varies from one lane to another lane of the sample carrier 104 and between different sample carriers 104 and thus the DNA fragment sizes cannot be determined simply from the acquisition time between the peaks in the DNA signals. In contrast, the ILS substance includes fragments with known sizes and migrates in a manner similar to the DNA fragments. Thus, although the spacing between the peaks in the ILS signal may stretch and shrink between lanes and runs, the ratio of acquisition times between the peaks in the ILS signal remains substantially constant. As such, a verified ILS signal from the ILS signal processor 116 is used to translate the acquisition times of the DNA fragment into DNA fragment sizes.

A DNA fragment identifier 120 identifies the DNA fragments based on fragment size and/or other information. The identified DNA fragments are used to determine the STR numbers as the DNA profile of the individual.

It is to be appreciated that the sample processing apparatus 102 may be configured to be a portable apparatus that can be readily carried by an operator or moved via wheels or the like. In another embodiment, the sample processing apparatus 102 is configured to be a stationary apparatus mounted to or placed on a table, the floor, etc. in a laboratory, office, or the like. In such a configuration, the sample processing apparatus 102 may be configured to remain at a particular location and process samples.

Figure 2:
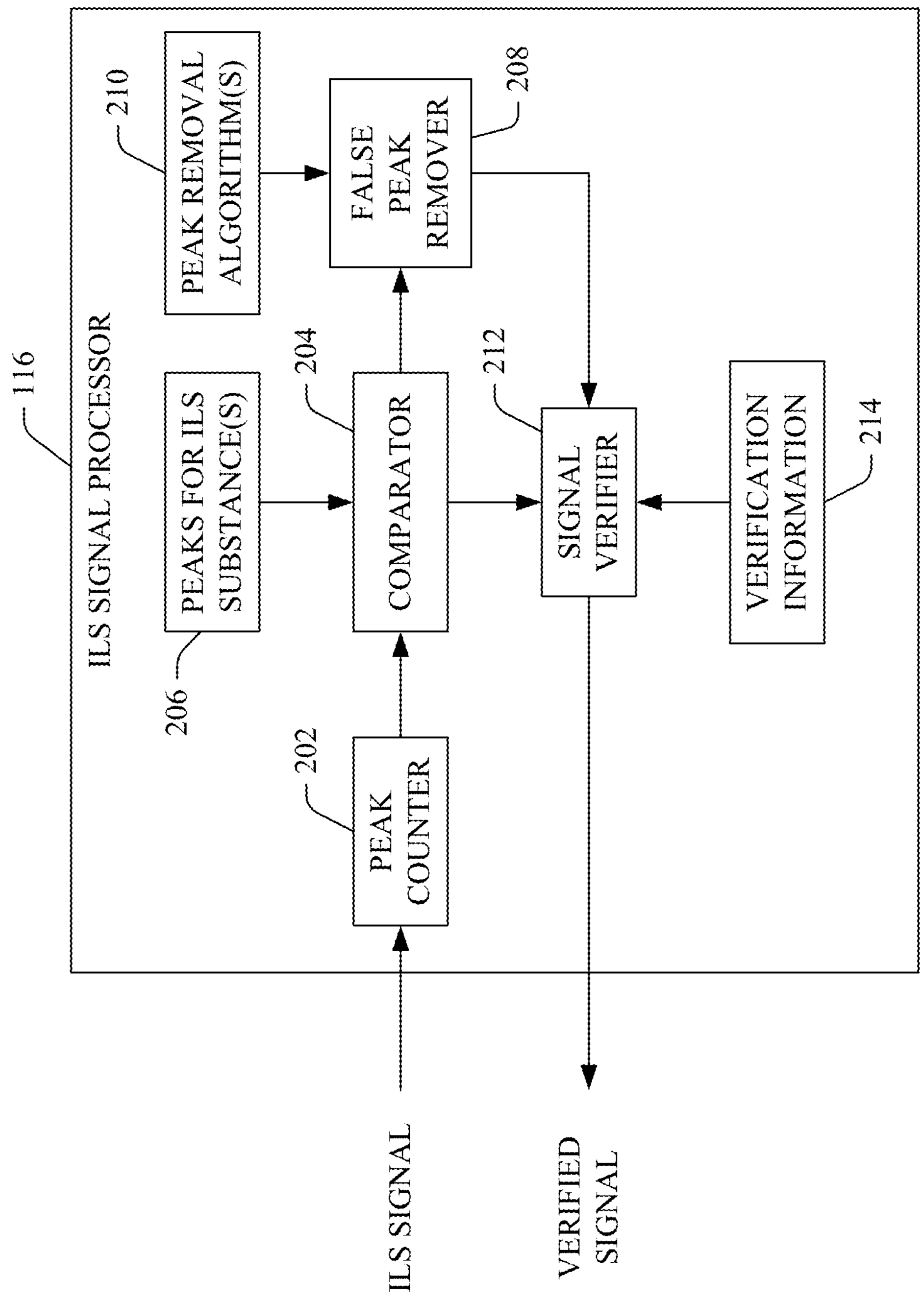
FIG. 2 illustrates an example ILS signal processor of the sample processing apparatus of FIG. 1.

FIG. 2 illustrates an example ILS signal processor 116. The illustrated example ILS signal processor 116 includes a peak counter 202 that detects and counts the number of peaks in the measured ILS signal. A comparator 204 compares the number of counted peaks with a predetermined number of peaks for the ILS substance 206. A false peak remover 208 identifies and removes false peaks from the ILS signal when the ILS signal includes false peaks. Generally, the false peak remover 208 is employed when the number of peaks in the ILS signal is greater than the number of peaks for the ILS substance 206. The peak remover 208 can use various algorithms, for example, one or more of the peak removal algorithms 210.

A signal verifier 212 verifies ILS signals having the correct number of peaks based on verification information 214, which includes information corresponding to the ratio of acquisition times between peaks of the ILS substance. Such verification includes verifying that the ILS signal only includes true peaks or that the ILS signal does not include any false peaks, and that the ILS signal does not include less peaks than the number of peaks for the ILS substance 206. The verification information 214 can be pre-stored in memory and used with multiple lanes of the sample carrier 104 and/or multiple sample carriers 104. The pre-stored information can be updated as needed. Furthermore, the information can be prepared manually or obtained from a detected reference signal with peak locations of normal and good-quality, e.g., from a signal with migration times close to the average migration time.

Figure 3:
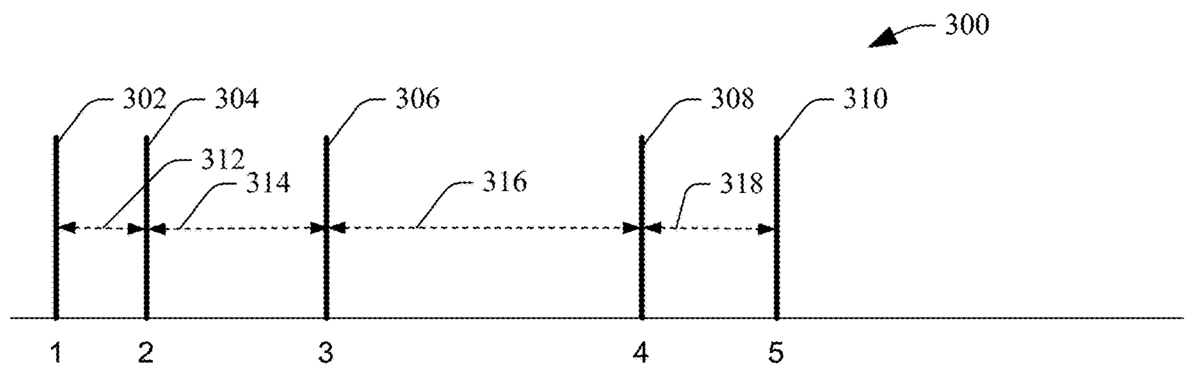
FIGS. 3-5 illustrate a non-limiting approach for verifying an ILS signal having a same number of peaks as reference ILS information, where the ILS signal and the reference ILS information have non-equally spaced peaks.
Figure 4:
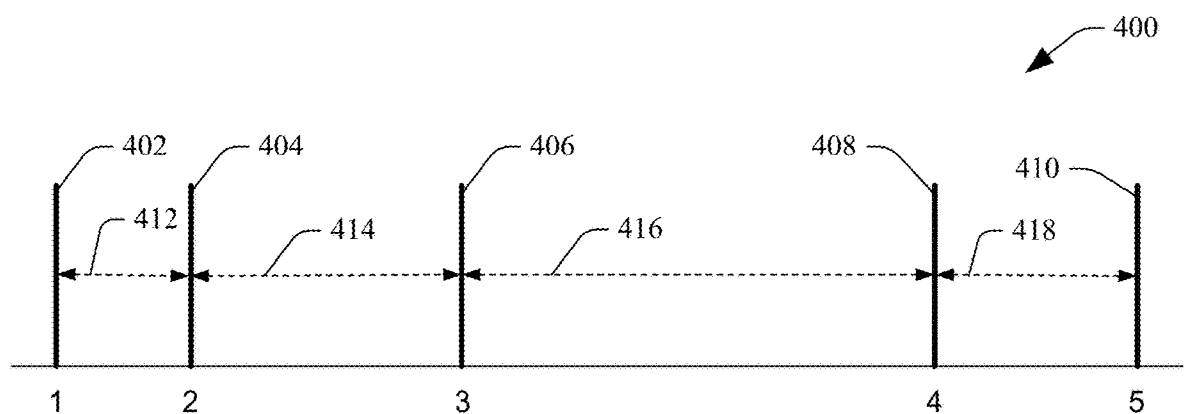
Figure 5:
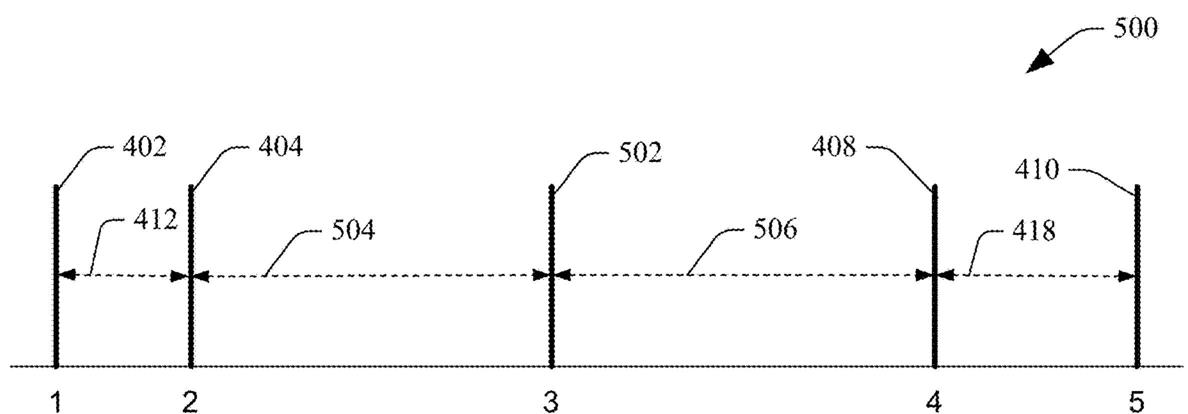

FIGS. 3-5 and the following discussion provide a non-limiting approach for verifying an ILS signal in which the ILS signal has a number of peaks equal to a number of peaks in the ILS reference information 214 for the ILS substance and the peaks in the ILS signal and the reference ILS information are not equally spaced.

Generally, the distribution of the peaks in the ILS signal may vary substantially. However, as long as the various parameters, such as electric field strength, temperature, and/or parameters remain substantially constant during electrophoresis, the distribution of the peaks remains in the same proportion. That is, the locations of the peaks may be shifted, but the separations between adjacent peaks are varied by the same ratio. In other words, the distribution of the ILS signal peaks may scale up or scale down in the time domain, but the pattern of the peak locations remains the same.

As such, an average value of the ratio of acquisition times between peaks for the ILS signal to the acquisition times between peaks in ILS reference information can be used as the expected ratio, and a deviation from this average ratio can be utilized to verify the ILS signal and/or a quality of the ILS signal based on a predetermined deviation threshold. For example, in one instance, if the maximum deviation from the average value is less than the predetermined deviation threshold, then all the ratios meet the expected ratio, and the ILS signal verifier 212 verifies the ILS likely has only true peaks and no false peaks. However, if the maximum deviation is equal to or greater than the predetermined deviation threshold, then one or more of the peaks are likely not true peaks but false peaks, and the signal verifier 212 rejects the ILS signal.

The ratio of the acquisition times ($R_i$) can be determined as shown in Equation 1:

$$R_i=(t_{i+1}-t_i)/(\tau_{i+1}-\tau_i), \qquad \text{Equation 1:}$$

where $t_i$ represents the acquisition time of peak i in the ILS signal, $\tau_i$ represents the acquisition time of peak i in the ILS reference information, and i=1, 2, . . . , N−1.

The average or mean value (μ) of the ratios can be determined as shown in Equation 2:

$$\mu=\frac{\left(\sum_{i=1}^{N-1} R_i\right)}{(N-1)}. \qquad \text{Equation 2}$$

As noted above, this value can be considered as the expected ratio.

The deviation ($D_i$) about the mean value can be determined as shown in Equation 3:

$$D_i=|\delta t/(\tau_{i+1}-\tau_i)|=|R_i-\mu|, \qquad \text{Equation 3:}$$

where δt represents a migration duration error and the migration duration is expressed in terms of the expected ratio and the error as shown in Equation 4:

$$t_{i+1}-t_i=\mu(\tau_{i+1}-\tau_i)+\delta t. \qquad \text{Equation 4:}$$

The deviation of Equation 3 can also be expressed relative to (or normalized by) its migration duration as shown in Equation 5:

$$D_i=|\delta t/(t_{i+1}-t_i)|=|R_i-\mu|/R_i \qquad \text{Equation 5:}$$

Equation 5 can be weighted based on known characteristics of the reference signal. For example, where some peaks are known to deviate more or less than other peaks, each peak may be weighted by a weighting factor $w_i$ between a value of zero (0) and one (1). When applying a weighting, Equation 5 can be expressed as shown in Equation 6:

$$D_i=(|R_i-\mu|*w_{i+1}*w_i)/R_i \qquad \text{Equation 6:}$$

Note that since $D_i$ is derived from peaks i+1 and i, it contains weight factors for both peaks.

Where the maximum deviation of the N−1 deviations is $D_k$ and the predetermined deviation threshold is $D_{max}$, Decision Criteria 1 can be used to determine whether all of the peaks are true peaks:

Decision Criteria 1

If $D_k<D_{max}$, then all peaks are likely to be true peaks, and the ILS signal is verified, and If $D_k\geq D_{max}$, then one or more peaks is likely to be a false peak, and ILS signal is rejected, wherein k represents the duration between peaks k and k+1.

The above is now described in connection with FIGS. 3-5. In the figures, the y-axis represents amplitude and the x-axis represents fragment size in units of base pairs, where a base pair is the size of a pair of DNA nucleotides. For explanatory purposes, $D_{max}$=0.1. In other embodiments, $D_{max}$ can be set to a lower or higher value.

FIG. 3 illustrates ILS reference information 300, which includes peaks 302, 304, 306, 308, and 310 with substantially the same amplitude, and non-equal acquisition times 312, 314, 316, and 318 between the peaks 302, 304, 306, 308, and 310. As discussed herein, the ILS reference information 300 can be from the verification information 214 (FIG. 2). Note that for a different ILS substance, the corresponding ILS reference information may be different than the ILS reference information 300.

FIG. 4 illustrates an example measured ILS signal 400 that includes peaks 402, 404, 406, 408, and 410 with substantially the same amplitude, and non-equal acquisition times 412, 414, 416, and 418 between the peaks 402, 404, 406, 408, and 410. From Equations 1-5 above, the ratios of the acquisition times of the ILS signal 400 to the acquisition times of the ILS reference information 300 ($R_1$, $R_2$, $R_3$, and $R_4$) are all about 1.50, the mean ratio ($\mu$) is about 1.5, and the maximum deviation ($D_k$) is about zero (0). In this instance, $D_k<D_{max}$ for all acquisition times, and the signal verifier 212 verifies the ILS signal 400 as only having true peaks. Note that the peaks of ILS signal 400 are spaced farther apart, relative to the peaks of the ILS reference information 300 of FIG. 3.

FIG. 5 illustrates an example ILS signal 500, which is similar to the measured reference signal 400 of FIG. 4 except that it is missing the true peak 406 and includes a false peak 502 and acquisition times 504 and 506 in place of acquisition times 414 and 416. As a consequence, $R_2$ is about 2.0 and $R_3$ is about 1.21, the mean ratio ($\mu$) is 1.55, and $D_2$=0.225 and $D_3$=0.281. In this instance, the maximum deviation $D_3$ is greater than $D_{max}$, and the signal verifier 212 rejects ILS signal 500.

FIGS. 6-10 and the following discussion provide a non-limiting approach for identifying and removing false peaks in a measured ILS having more peaks than the number of peaks in the ILS reference information 214 for the ILS substance. Similar to FIGS. 3-5, in these figures, the y-axis represents amplitude and the x-axis represents fragment size in units of base pairs.

For this example, the ILS signal includes N+M peaks, where N is the number of peaks in the ILS reference information 214 and M is the number of peaks in excess of the number of peaks in the ILS reference information 214.

Where M=1, one of the peaks is removed from the ILS signal leaving N peaks, and N−1 deviations are determined based on Equations 3 or 5 for the N−1 acquisition times between the N peaks as described above. This is repeated for the other peaks as well, resulting in a total of N+1 candidate ILS signals and, thus, N+1 maximum deviations (one maximum deviation for each of the N+1 candidate ILS signals).

Where M=2, a set of two peaks is removed from the ILS signal leaving N peaks, and N−1 deviations are determined based on Equations 3 or 5 for the N−1 acquisition times between the N peaks as described above. This is repeated for the other sets of two peaks as well, resulting in a total of (N+2)×(N+1)/2 candidate ILS signals and, thus, (N+2)×(N+1)/2 maximum deviations.

More generally, the number of candidate ILS signals and maximum deviations can be determined through the following:

$$\frac{(N+M)!}{(M!)(N!)},$$

where N is the number of peaks in the ILS reference information and M is the number of peaks in the ILS signal in excess of N. The signal verifier 212 applies Decision Criteria 1 above to the candidate ILS signal with the lowest maximum deviation.

The above approach is now described in connection with FIGS. 3 (described above) and 6-10. For explanatory purposes and sake of brevity, N=5, M=1, and $D_{max}$=0.1, although N, M and/or $D_{max}$ can be lower or higher in other embodiments. With N=5 and M=1, there are six (6) candidate ILS signals. For this example, the reference ILS information 300 of FIG. 3 is used as the reference ILS information.

Figure 6:
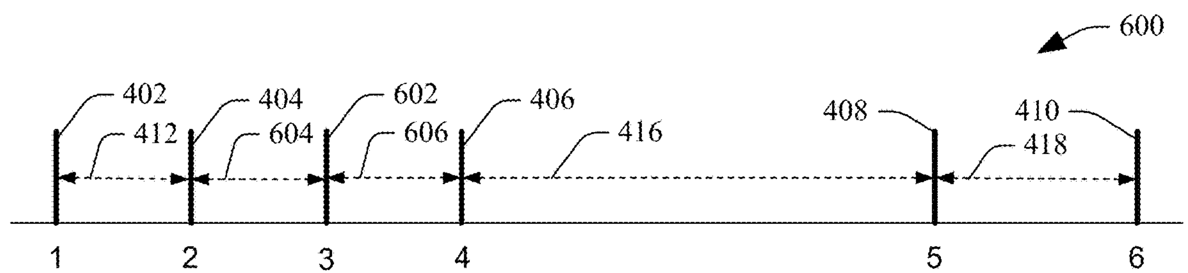
FIGS. 6-10 illustrate a non-limiting approach for identifying and removing false peaks in an ILS signal having more peaks than the number of peaks in reference ILS information, where the ILS signal and the reference ILS information have non-equally spaced peaks.

FIG. 6 illustrates an example ILS signal 600. The ILS signal 600 is similar to the ILS signal 400 of FIG. 4 except that it includes a false peak 602 between peaks 404 and 406, which splits the acquisition time 314 into an acquisition time 604 from peak 404 to peak 602 and an acquisition time 606 from peak 602 to peak 406.

Figure 7:
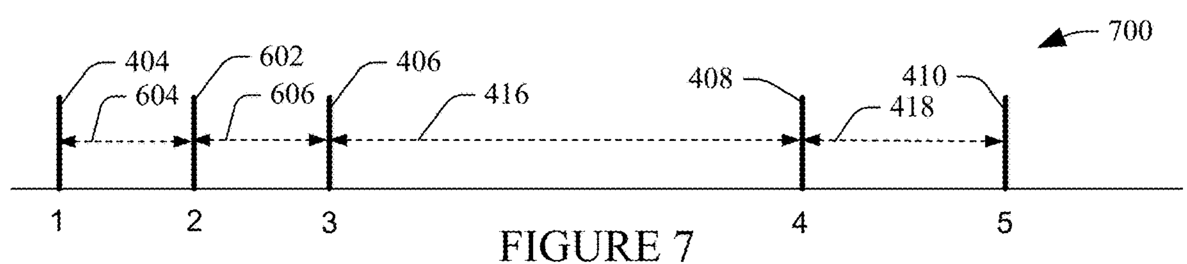
Figure 8:
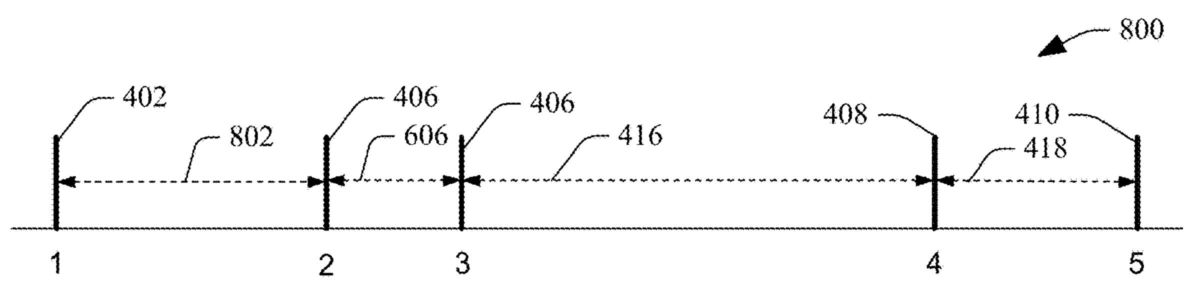

FIG. 7 illustrates a candidate ILS signal 700 in which the peak 402 is removed from ILS signal 600 and the remaining peaks are shifted so that the first peak aligns with the first peak of the reference ILS information 300 of FIG. 3. For the candidate signal 700, the maximum deviation $D_k$ for the ratio of acquisition time 606 to the acquisition time 314 is greater than $A_{max}$. In FIG. 8 illustrates a candidate signal 800 in which the peak 404 is removed from ILS signal 600, and acquisition times 412 and 604 combine to form acquisition time 802. Likewise, the maximum deviation $D_k$ for the ratio of acquisition time 802 to the acquisition time 312 is greater than $D_{max}$.

Figure 9:
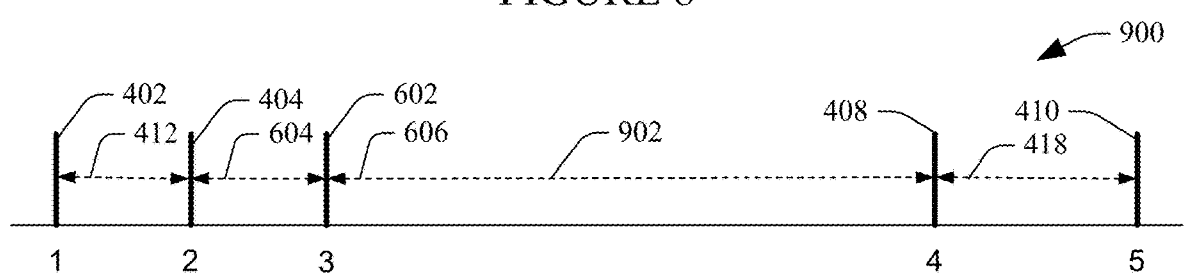
Figure 10:
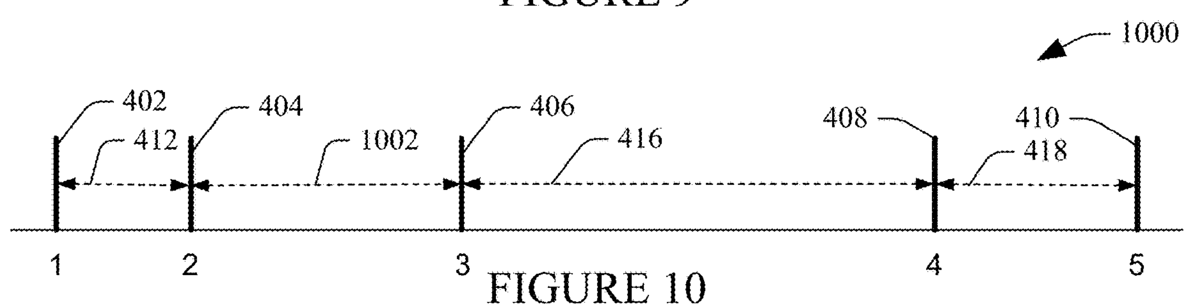

FIG. 9 illustrates a candidate ILS signal 900 in which the peak 406 is removed from the ILS signal 600, and acquisition times 606 and 414 combine to form acquisition time 902. This results in a maximum deviation $D_k$ for the ratio of acquisition time 604 to the acquisition time 314 or for the ratio of acquisition time 902 to the acquisition time 316 that is greater than $D_{max}$. FIG. 10 illustrates a candidate ILS signal 1000 in which the false peak 602 is removed from the ILS signal 600, and acquisition times 602 and 604 combine to form acquisition time 1002, which is equal to acquisition time 314. In this instance, the reference ILS information maps 1:$\alpha$1, where $\alpha$ is a scaling factor, with the ILS signal 1000, and the maximum deviation $D_k$ is less that $D_{max}$.

In this example, the ILS verifier 212 rejects the ILS signals 700, 800 and 900 and verifies the ILS signal 1000.

In the above example, the reference ILS information 300 of FIG. 3 has non-equally spaced peaks, or different acquisition times. If the reference ILS information has equally spaced peaks and the same acquisition times, the above approach can be used to identify false peaks between the first and last true peaks.

FIGS. 11-15 illustrate an example for removing a false peak where the reference ILS information includes substantially equal spaced peaks with a least two different and distinct amplitudes. Like FIGS. 3-10, the y-axis represents amplitude and the x-axis represents fragment size in units of base pairs. In this embodiment, the higher amplitude peaks are first matched and then the lower amplitude peaks are matched. One of the commonly used ILS substances has similar nature as shown in this example.

Figure 11:
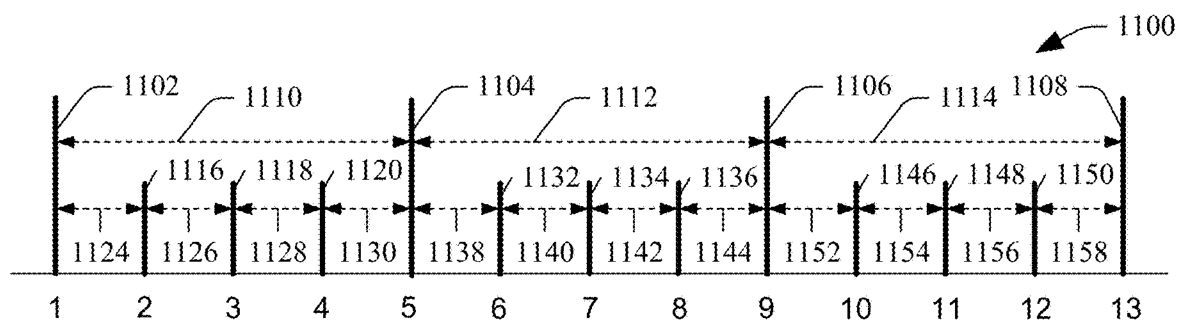
FIGS. 11-15 illustrate a non-limiting approach for identifying and removing false peaks in an ILS signal having more peaks than the number of peaks in reference ILS information, where the ILS signal and the reference ILS information have equally spaced peaks and at least two different and distinct peak amplitudes.

FIG. 11 illustrates reference ILS information 1100 having four substantially equally spaced higher amplitude peaks 1102, 1104, 1106, and 1108, and acquisition times of 1110, 1112, and 1114. Between higher amplitude peaks 1102 and 1104 are three equally spaced smaller amplitude peaks 1116, 1118 and 1120, and acquisition times 1124, 1126, 1128, and 1130. Between higher amplitude peaks 1104 and 1106 are three equally spaced smaller amplitude peaks 1132, 1134 and 1136, and acquisition times 1138, 1140, 1142, and 1144. Between higher amplitude peaks 1106 and 1108 are three equally spaced smaller amplitude peaks 1146, 1148 and 1150, and acquisition times 1152, 1154, 1156, and 1158.

Figure 12:
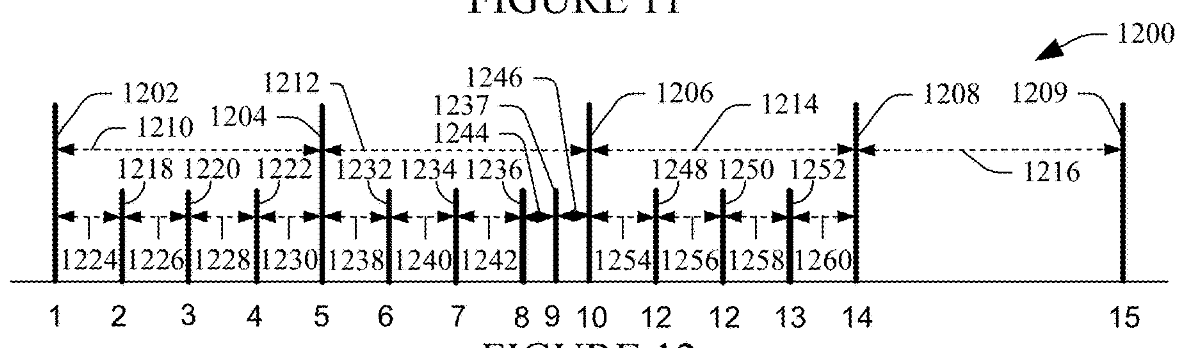
Figure 13:
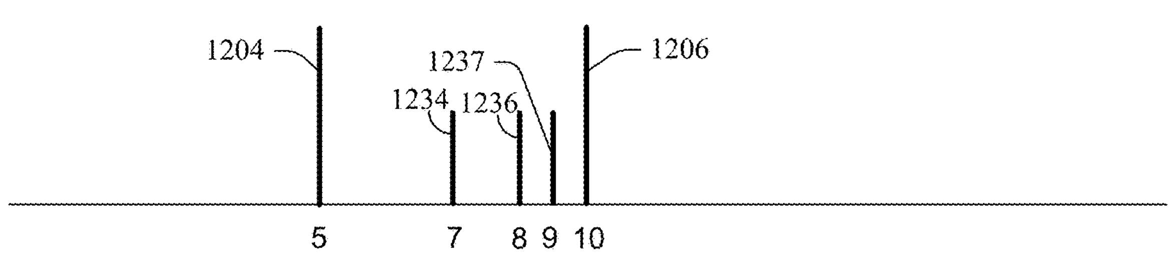
Figure 14:
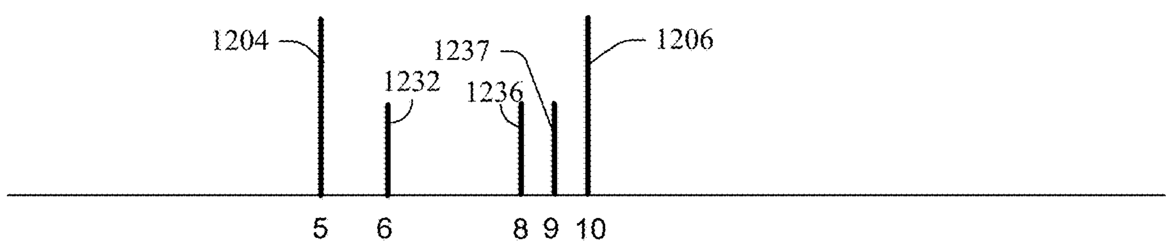
Figure 15:
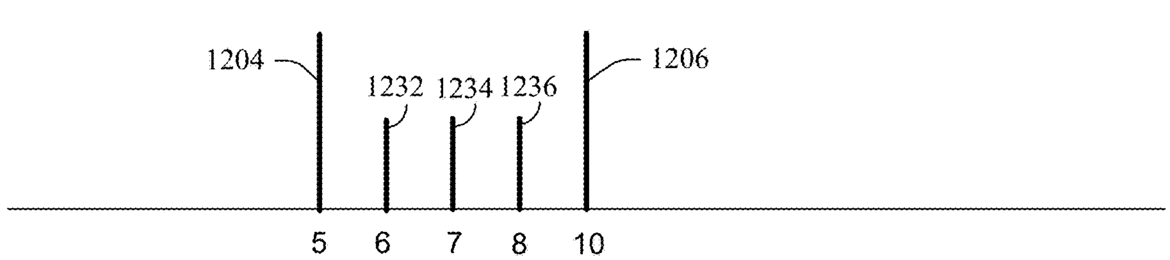

FIG. 12 illustrates an ILS signal 1200 that has a false larger amplitude peak and a false lower amplitude peak. More specifically, the signal 1200 has five substantially equally spaced higher amplitude peaks including four true peaks 1202, 1204, 1206 and 1208, and a false peak 1209, and acquisition times of 1210, 1212, 1214 and 1216. Between higher amplitude peaks 1202 and 1204 are three equally spaced smaller amplitude peaks 1218, 1220 and 1222, and acquisition times 1224, 1226, 1228, and 1230. Between higher amplitude peaks 1204 and 1206 are three equally spaced smaller amplitude peaks 1232, 1234 and 1236 and a false peak 1237 between the smaller peak 1236 and the larger peak 1206, and acquisition times 1238, 1240, 1242, 1244, and 1246. Between higher amplitude peaks 1206 and 1208 are three equally spaced smaller amplitude peaks 1248, 1250 and 1252, and acquisition times 1254, 1256, 1258, and 1260.

Initially, the higher amplitude peaks 1102, 1104, 1106 and 1108 of the reference ILS information are matched against the higher amplitude peaks 1202, 1204, 1206, 1208 and 1209 of the ILS signal 1200. Dropping the peak 1202 or the peak 1209 results in a maximum deviation of about zero, which is lower than the predetermined threshold, whereas dropping the peaks 1104 or 1106 results in a maximum deviation that is greater than the predetermined threshold. The smaller amplitude peaks are then used to select which of peak 1202 or 1209 to drop. When peak 1202 is removed, there are extra smaller amplitude peaks 1218, 1220, 1222 before the larger amplitude peak 1204 and there are no smaller amplitude peaks between the larger amplitude peaks 1108 and 1109, and this rejected. When the larger amplitude peak 1209 is removed, there are three equally spaced smaller amplitude peaks between the larger amplitude peaks 1202 and 1204, and this is accepted.

Next, the lower amplitude peaks 1132, 1134 and 1136 of the reference ILS information are matched against the lower amplitude peaks 1232, 1234, 1236, and 1237 of the ILS signal 1200. Dropping any of the peaks 1232 (FIG. 13), 1234 (FIG. 13) or 1236 will result in a maximum deviation that is greater than the predetermined threshold, and the corresponding candidate ILS signals are rejected. However, dropping the peak 1237 (FIG. 15), results in a maximum deviation about zero, which is lower than the predetermined threshold, and the candidate signal with peak 1237 removed is identified as the ILS signal.

Figure 16:
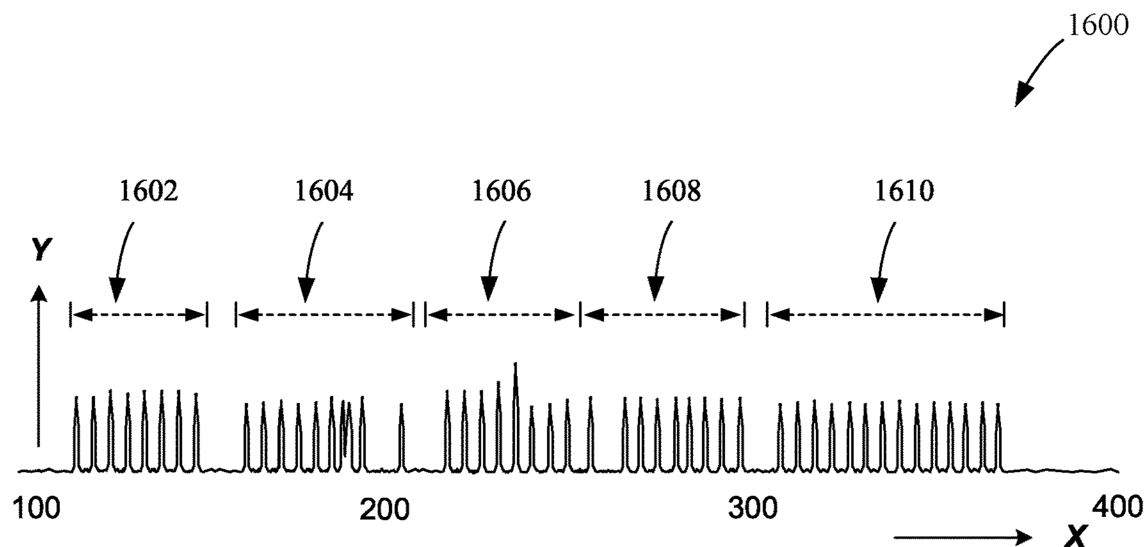
FIG. 16 illustrates a non-limiting approach for identifying and removing false peaks in an allele ladder signal and verifying the ladder signal.

The above described approaches can also be used with allelic ladder signals as shown in connection with FIG. 16 in which the y-axis represents amplitude and the x-axis represents fragment size in units of base pairs. In FIG. 16, the ladder signal 1600 is divided into multiple regions 1602, 1604, 1606, 1608 and 1610 to match specific markers. In each region, most of the peaks are equally spaced. However, the duration between adjacent regions is distinctly longer than the duration between two peaks in the region. Overall, the peaks in the ladder signal are not equally spaced. The nature of the ladder is also different from the ILS signal.

In general, the ladder signal contains more peaks and artifacts than the ILS signal, and some of the peaks in the ladder signal can be very weak and thus it is likely that the ladder signal may miss some peaks. The acquisition times of all the peaks in the ladder signal can be estimated within certain accuracy based on the translation from the processed ILS signal. Thus, missing peaks can be found and interpolated by some other means. After fixing the missing peaks, the approaches described herein can be used to find and remove false peaks and to verify the integrity of the ladder signal.

Figure 17:
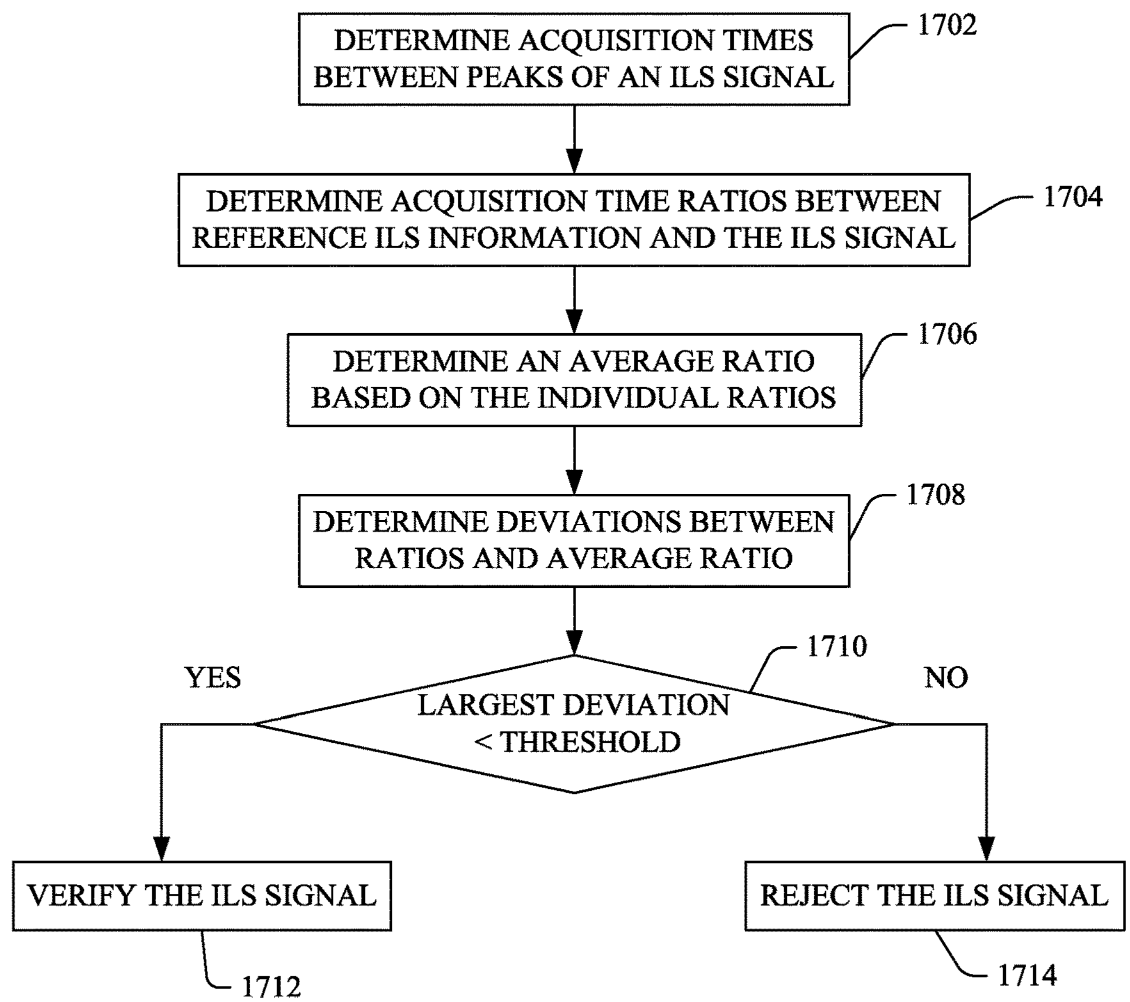
FIG. 17 illustrates a method for verifying that the peaks in an ILS signal are true peaks based on reference ILS information, where the number of peaks in the ILS signal and the reference ILS information are the same.

FIG. 17 illustrates a method for verifying that the peaks in an ILS signal are true peaks where the number of peaks in the ILS signal and the reference ILS information are the same.

At 1702, acquisition times between peaks in an ILS signal are determined.

At 1704, ratios between acquisition times between peaks in reference ILS information and the acquisition times between the peaks in the ILS signal are determined.

At 1706, an average ratio is determined based on the ratios.

At 1708, deviations between each of the ratios and the average ratio are determined.

At 1710, the largest of the deviation is compared against predetermined deviation threshold.

At 1712, if the largest deviation satisfies the threshold, the ILS signal is verified.

At 1714, if the largest deviation does not satisfy the threshold, the ILS signal is rejected.

Figure 18:
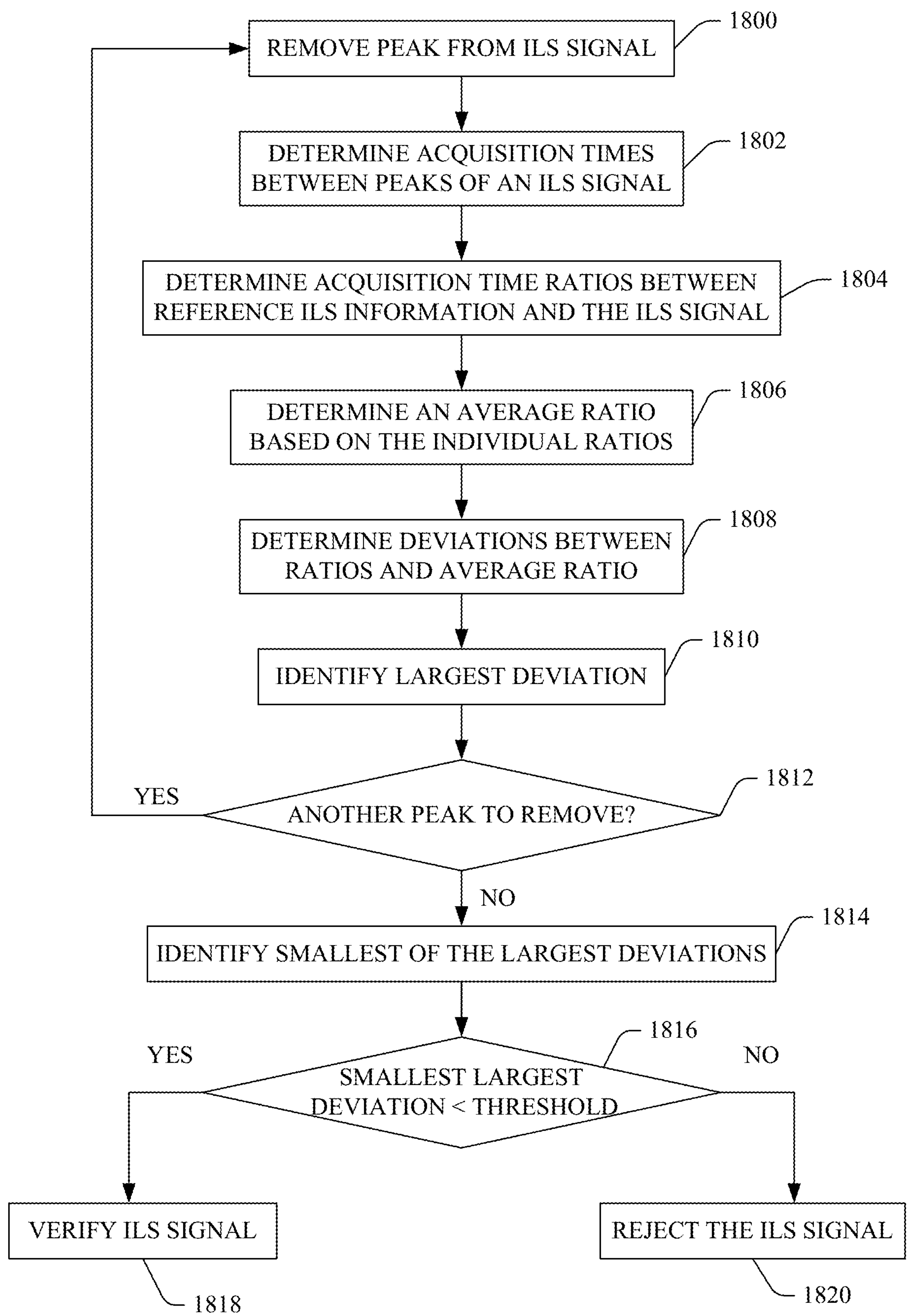
FIG. 18 illustrates a method for removing one or more false peaks from an ILS signal having one or more peaks than the number of peaks in reference ILS information.

FIG. 18 illustrates a method for removing one or more false peaks from an ILS signal having one or more peaks than the number of peaks in reference ILS information. For sake of brevity and explanatory purposes, the following is described in connection with an ILS signal having one false peak. However, as described herein, the multiple false peaks can be removed where the ILS signal has multiple false peaks.

At 1800, one of the peaks is removed from the ILS signal.

At 1802, acquisition times between peaks in an ILS signal are determined.

At 1804, ratios of acquisition times between peaks in reference ILS information to the acquisition times between the peaks in the ILS signal are determined.

At 1806, an average ratio is determined based on the ratios.

At 1808, deviations between each of the ratios and the average ratio are determined. As described herein, the deviations may or may not be weighted deviations.

At 1810, the largest of the deviations is identified.

At 1812, it is determined whether another combination of peaks is available to be processed.

If so, then acts 1800 to 1812 are repeated for an ILS signal with a different one of the peaks removed.

If not, then at 1814, the smallest of the identified largest deviations is identified.

At 1816, the smallest of the largest deviations is compared against predetermined deviation threshold.

At 1818, if the smallest of the largest deviations satisfies the threshold, the ILS signal is verified.

At 1820, if the smallest of the largest deviations does not satisfy the threshold, the ILS signal is rejected.

As described herein, the above method can be applied to the case where the ILS signal has M peaks in excess of the number of peaks in the reference ILS information.

Figure 19:
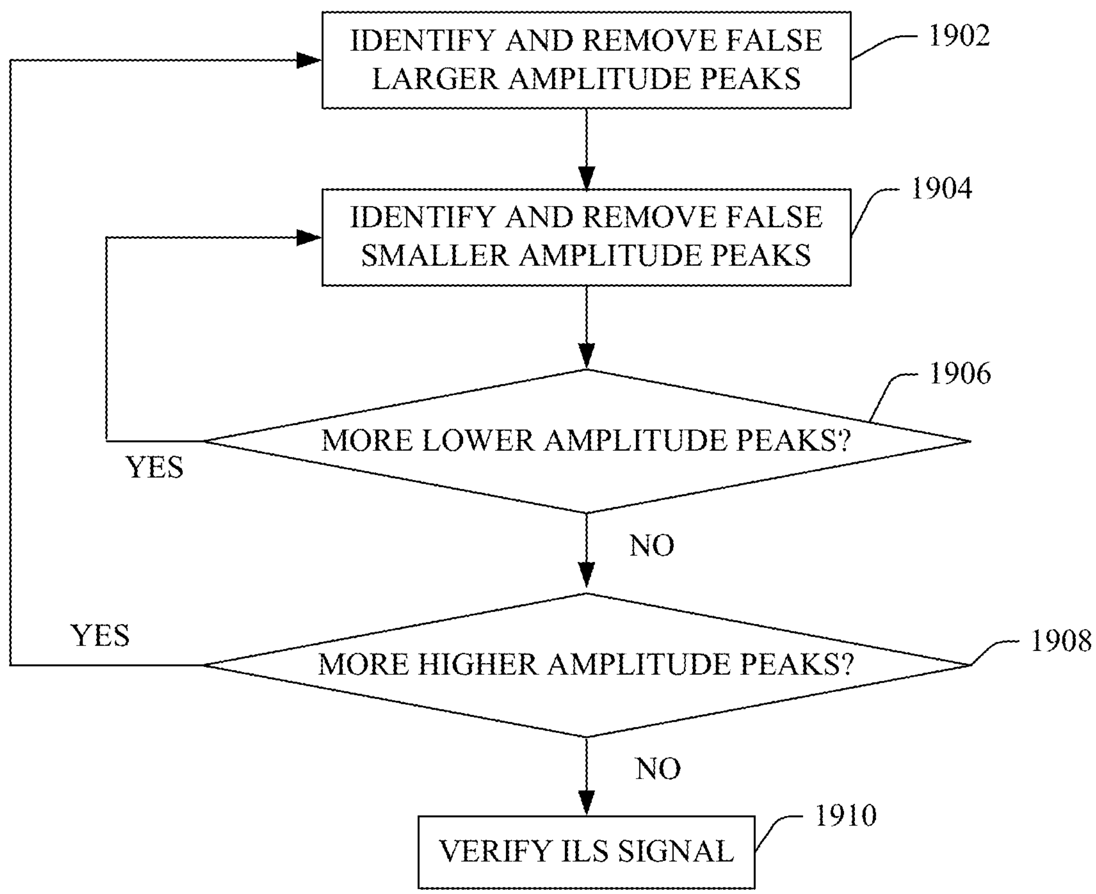
FIG. 19 illustrates a method for removing one or more false peaks from an ILS signal having one or more peaks than the number of peaks in reference ILS information, where the ILS signal and the reference ILS information have at least two different and distinct amplitudes.

FIG. 19 illustrates a method for removing one or more false peaks from an ILS signal having one or more peaks than the number of peaks in reference ILS information, where the ILS signal and the reference ILS information have at least two different and distinct amplitudes and the ILS signal includes at least one false higher amplitude peak and at least one false smaller amplitude peak.

At 1902, the larger amplitude peaks of the ILS signal are matched against the larger amplitude peaks of the reference ILS information, and a candidate ILS signal is identified based on the resulting acquisition time ratio deviations and dropping larger peaks if it has more higher amplitude peaks than the reference ILS information, as described herein. Where the peaks in the ILS signal are equally spaced and the false peak is either before the first peak or after the last peak, the smaller amplitude peaks can also be used to identify the candidate ILS signal.

At 1904, the smaller amplitude peaks of the ILS signal are matched against the smaller amplitude peaks of the reference ILS information and the candidate ILS signal is further refined based on the resulting acquisition time ratio deviations and dropping smaller peaks if it has more smaller amplitude peaks than the reference ILS information, as described herein.

At 1906, it is determined whether more lower-amplitude peaks are to be dropped. If so, act 1904 is repeated.

If not, then at 1908 it is determined whether more higher-amplitude peaks are to be dropped. If so, act 1902 is repeated.

If not, then at 1910, the signal is verified.

In other embodiments, the ILS signal may only have one or more false higher amplitude peaks or one or more false lower amplitude peaks.

Figure 20:
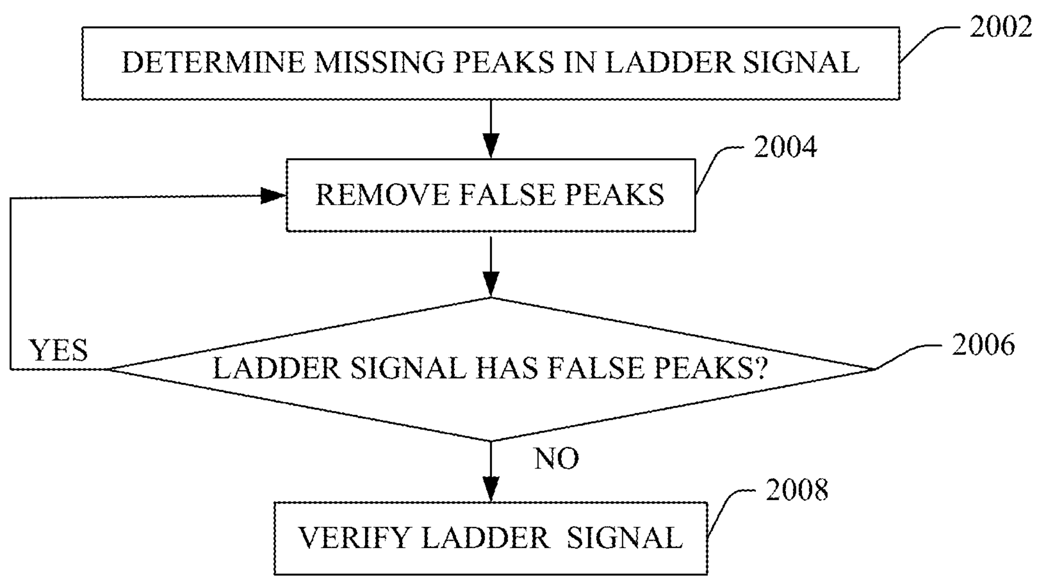
FIG. 20 illustrates a method for identifying and removing one or more false peaks from an allele ladder signal and/or verifying the ladder signal.

FIG. 20 illustrates a method for identifying and removing one or more false peaks from a allelic ladder signal and/or verifying the ladder signal.

At 2002, determine missing peaks in a ladder signal.

At 2004, the ladder signal is matched against the reference ladder information, and a candidate ladder signal is identified based on the resulting acquisition time ratio deviations and dropping selected false peaks if it has more peaks than the reference ladder information, as described herein.

At 2006, it is determine whether more false peaks are to be removed. If so, then act 2004 is repeated.

If not, then at 2008 the ladder signal is verified as including only true peaks, as described herein.

It is to be appreciated that the methods herein can be implemented via one or more processor of one or more computing systems executing one or more computer readable and/or executable instructions stored on computer storage medium such as memory local to or remote from the one or more computing systems.

Figure 21:
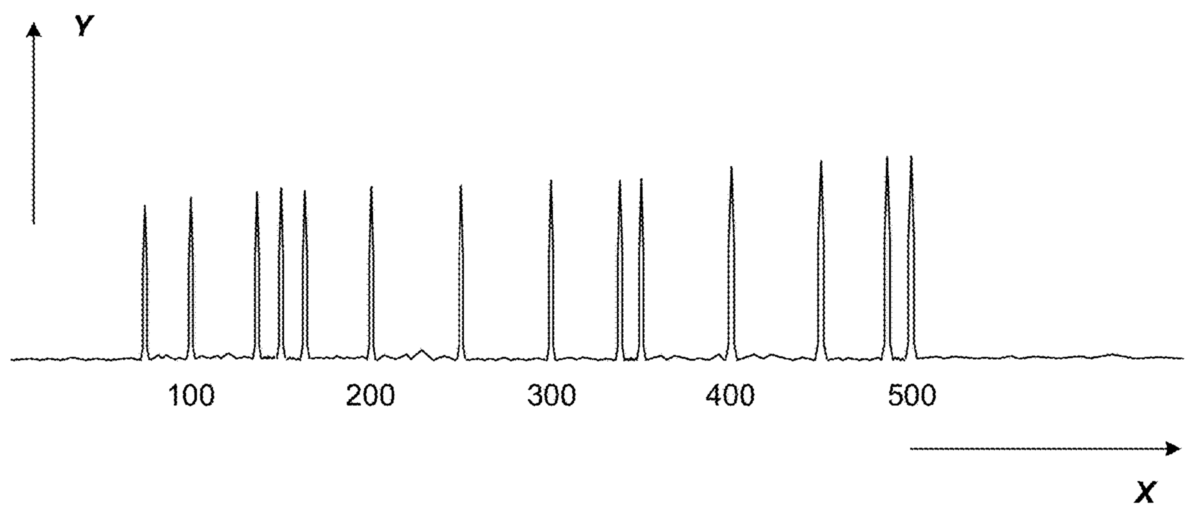
FIG. 21 illustrates a typical ILS signal.

FIG. 21 illustrates a typical ILS signal. The y-axis represents amplitude and the x-axis represents fragment size in units of base pairs, where a base pair is the size of a pair of DNA nucleotides.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method, comprising:

receiving a sample at a sample processing apparatus;

separating, at the sample processing apparatus, the sample into fragments;

generating, with an optical reader of the sample processing apparatus, an output indicative of light sensed by the optical reader where the light is emitted by dyes in dye labeled and separated fragments of the sample in response to the optical reader directing a light beam of a predetermined wavelength range at the dye labeled and separated fragments;

identifying, with a processor of the sample processing apparatus, a signal of the output that includes an Internal Lane Standard (ILS) signal, wherein the ILS signal has a first number of peaks and the first number of peaks are unequally spaced with respect to each other;

determining, with the processor, acquisition times between peaks of the ILS signal;

obtaining, with the processor, acquisition times between peaks in reference ILS information for the ILS signal, wherein the reference ILS information has a second number of peaks and the second number of peaks are unequally spaced with respect to each other, the second number of peaks is the same as the first number of peaks, and a spacing of the peaks in the ILS signal is different than a spacing in the reference ILS information;

determining, with the processor, ratios of the ILS signal acquisition times to the reference ILS information acquisition times;

verifying, with the processor, that the ILS signal includes only true peaks based on the ratios;

translating, at the sample processing apparatus, acquisition times of the ILS signal into fragment sizes based on a verified ILS signal; and identifying DNA fragments based on the fragment sizes.

2. The method of claim 1, wherein verifying comprises:

determining an average ratio based on the ratios;

determining deviations of the ratios from the average ratio;

identifying the largest of the deviations; and verifying the ILS signal includes only true peaks in response to the largest deviation satisfying a predetermined deviation threshold range.

3. The method of claim 2, further comprising:

rejecting the ILS signal in response to the largest deviation not satisfying the predetermined deviation threshold range.

4. The method of claim 2, further comprising:

weighting the deviations by weighting factors corresponding to peaks of the respective acquisition times.

5. The method of claim 2, further comprising:

normalizing deviations by corresponding ratios.

6. The method of claim 2, further comprising:

determining a quality of the verified ILS signal based on the deviations.

7. The method of claim 1, wherein the ILS signal and the reference ILS information include non-equally spaced peaks.

8. The method of claim 1, wherein the ILS signal is an allelic ladder signal instead, and further comprising: at least one of verifying the peaks in the ladder signal are true peaks or identifying and removing false peaks in the ladder signal.

9. A method, comprising:

receiving a sample at a sample processing apparatus;

separating, at the sample processing apparatus, the sample into fragments;

generating, with an optical reader of the sample processing apparatus, an output indicative of light sensed by the optical reader where the light is emitted by dyes in dye labeled and separated fragments of the sample in response to the optical reader directing a light beam of a predetermined wavelength range at the dye labeled and separated fragments;

identifying, with a processor of the sample processing apparatus, a signal of the output that includes an Internal Lane Standard (ILS) signal;

determining, with the processor, a number of peaks in the ILS signal, wherein the ILS signal has a first number of peaks and the first number of peaks includes at least one false peak;

obtaining, with the processor, a number of peaks in reference ILS information, wherein the reference ILS information has a second number of peaks, and the first number of peaks is greater than the second number of peaks;

determining, with the processor, the ILS signal includes one or more false peaks in response to the first number of peaks in the ILS signal being greater than the second number of peaks from the reference ILS information;

determining, with the processor, acquisition times between peaks of the ILS signal;

obtaining, with the processor, acquisition times between peaks in the reference ILS information;

identifying the one or more false peaks based on ratios of the ILS signal acquisition times to the reference ILS information acquisition times;

removing, with the processor, the one or more false peaks from the ILS signal;

translating, at the sample processing apparatus, the acquisition times of the ILS signal into fragment sizes based on the ILS signal with the removed one or more false peaks; and identifying DNA fragments based on the fragment sizes.

10. The method of claim 9, wherein identifying the one or more false peaks comprises:

removing different sets of peaks of the ILS signal, wherein for each removed set the number of peaks in the ILS signal equals the number of peaks from the reference ILS information;

calculating, for each removed set of peaks, deviations for the ratios of the acquisition times between peaks of the processed ILS signal and the acquisition times between the peaks in the reference ILS information; and identifying the one or more false peaks as the set of peaks corresponding to the processed ILS signal having the lowest maximum deviation.

11. The method of 9, further comprising:

determining acquisition times between the peaks of the ILS signal;

obtaining acquisition times between the peaks in reference ILS information for the ILS signal;

determining ratios of the ILS signal acquisition times to the reference ILS information acquisition times; and verifying that the ILS signal includes only true peaks based on the ratios.

12. The method of claim 11, further comprising:

determining an average ratio based on the ratios;

determining deviations of the ratios from the average ratio;

identifying the largest of the deviations; and verifying the ILS signal includes only true peaks in response to the largest deviation satisfying a predetermined deviation threshold range.

13. The method of claim 12, further comprising:

rejecting the ILS signal in response to the largest deviation not satisfying the predetermined deviation threshold range.

14. The method of claim 12, further comprising:

rejecting the ILS signal in response to the largest deviation not satisfying the predetermined deviation threshold range.

15. The method of claim 11, further comprising:

determining an average ratio based on the ratios;

determining deviations of the ratios from the average ratio;

identifying the largest of the deviations; and verifying the ILS signal includes only true peaks in response to the largest deviation satisfying a predetermined deviation threshold range.

16. A method, comprising:

receiving a sample at a sample processing apparatus;

separating, at the sample processing apparatus, the sample into fragments;

generating, with an optical reader of the sample processing apparatus, an output indicative of light sensed by the optical reader where the light is emitted by dyes in dye labeled and separated fragments of the sample in response to the optical reader directing a light beam of a predetermined wavelength range at the dye labeled and separated fragments;

identifying, with a processor of the sample processing apparatus, a signal of the output that includes an Internal Lane Standard (ILS) signal;

wherein each of the ILS signal and the reference ILS information includes equally spaced peaks having at least first and second amplitudes, and a number of peaks having a first amplitude is less than a number of the peaks having a second amplitude, wherein the first amplitude is greater than or less than the second amplitude;

verifying, with the processor, the peaks with the first amplitude before and independent of the peaks with the second amplitude or verifying the peaks with the second amplitude before and independent of the peaks with the first amplitude;

translating, at the sample processing apparatus, acquisition times of the ILS signal into fragment sizes based on a verified ILS signal; and identifying DNA fragments based on the fragment sizes.

17. The method of 16, where the first amplitude is greater than the second amplitude and the peaks with the first amplitude are verified first, further comprising:

selecting the peaks with the second amplitude based on the verified peaks with the first amplitude; and verifying the peaks with the second amplitude between successive peaks with the first amplitude.

18. The method of 16, where the second amplitude is greater than the first amplitude and the peaks with the second amplitude are verified first, further comprising:

selecting the peaks with the first amplitude based on the verified peaks with the second amplitude; and verifying the peaks with the first amplitude peaks between successive peaks with the second amplitude.

19. The method of 12, further comprising:

determining acquisition times between the peaks of the ILS signal;

obtaining acquisition times between the peaks in reference ILS information for the ILS signal;

determining ratios of the ILS signal acquisition times to the reference ILS information acquisition times; and verifying that the ILS signal includes only true peaks based on the ratios.

* * * * *

UNITED STATES PATENT AND TRADEMARK OFFICE

CERTIFICATE OF CORRECTION

PATENT NO. : 10,503,573 B2
APPLICATION NO. : 13/704007
DATED : December 10, 2019
INVENTOR(S) : Ching Ming Lai It is certified that error appears in the above-identified patent and that said Letters Patent is hereby corrected as shown below:

In the Specification

| | | |
|---|---|---|
| Column 1, | Line 52, | change "sub stance." to --substance.-- |
| Column 4, | Line 12, | change "sub stance." to --substance.-- |
| Column 8, | Line 13, | change "$A_{max}$." to --$D_{max}$.-- |
| Column 8, | Line 31, | change "that" to --than-- |

Signed and Sealed this
Twenty-eighth Day of January, 2020

Andrei Iancu
*Director of the United States Patent and Trademark Office*